United States Patent [19]

Powell et al.

[11] Patent Number: 4,771,776
[45] Date of Patent: Sep. 20, 1988

[54] DILATATION CATHETER WITH ANGLED BALLOON AND METHOD

[75] Inventors: Elizabeth A. Powell, Belmont; Andree L. Barker, Mountain View, both of Calif.

[73] Assignee: Advanced Cardiovascular Systems, Inc., Mountain View, Calif.

[21] Appl. No.: 652

[22] Filed: Jan. 6, 1987

[51] Int. Cl.[4] .......................................... A61M 29/02
[52] U.S. Cl. .................................... 128/344; 604/96; 604/281
[58] Field of Search .................... 128/344, 10; 604/93, 604/96, 99, 103, 118, 280, 281

[56] References Cited

U.S. PATENT DOCUMENTS

| | | | |
|---|---|---|---|
| 923,303 | 6/1909 | Shults | 128/344 |
| 4,214,593 | 7/1980 | Imbruce et al. | 604/96 |
| 4,349,029 | 9/1982 | Mott | 604/96 |
| 4,456,000 | 6/1984 | Schjeldahl et al. | 128/10 |
| 4,571,239 | 2/1986 | Heyman | 604/280 |
| 4,589,868 | 5/1986 | Dretler | 604/96 |
| 4,597,755 | 7/1986 | Samson et al. | 604/96 |

*Primary Examiner*—C. Fred Rosenbaum
*Assistant Examiner*—Gene B. Kartchner
*Attorney, Agent, or Firm*—Fulwider, Patton, Rieber, Lee & Utecht

[57] ABSTRACT

Angled balloon dilatation catheter having a flexible elongate tubular member with first and second lumens extending therethrough and with proximal and distal extremities. An angled balloon is carried by the distal extremity of the tubular member. The elongate tubular member has a tubular element extending through the balloon. The first lumen extends through the tubular element and is capable of receiving a guide wire so that the guide wire extends therethrough. The second lumen is in communication with the interior of the angled balloon for inflating and deflating the balloon. The balloon subtends a predetermined interior angle.

15 Claims, 2 Drawing Sheets

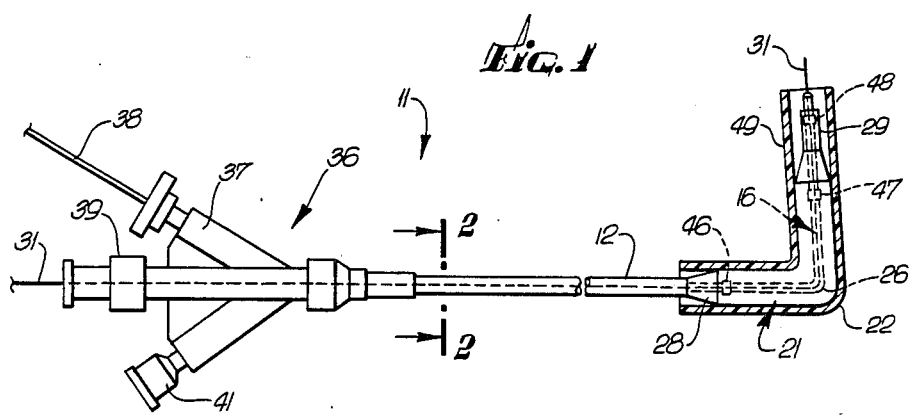
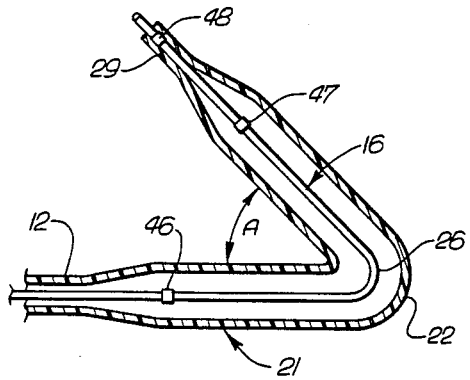
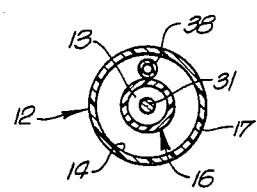
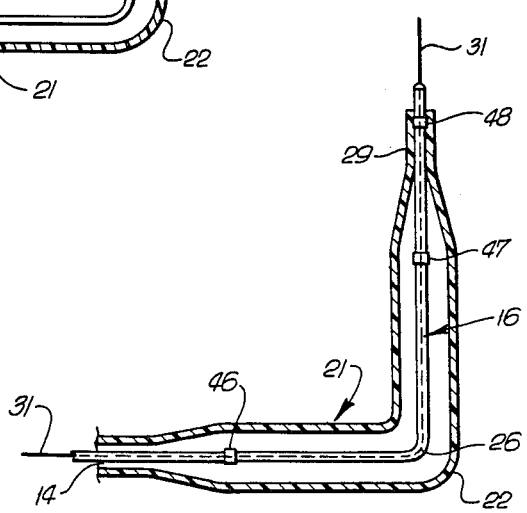

DILATATION CATHETER WITH ANGLED BALLOON AND METHOD

This invention relates to a dilatation catheter with angled balloon and method.

In angioplasty procedures, it has been found that there are certain vessels in the heart and in other parts of the body such as the kidneys which are difficult to treat with conventional straight balloon dilatation catheters. This is particularly true where the stenosis occurs in a bend in the vessel which makes it very difficult to treat the stenosis. There is therefore a need for a new and improved dilatation catheter and method which can be utilized for treating stenoses of that type.

In general, it is an object of the present invention to provide a dilatation catheter having an angled balloon and a method.

Another object of the invention is to provide a dilatation catheter and method of the above character which can be used for treating stenoses which occur at an angle.

Another object of the invention is to provide a dilatation catheter and method of the above character in which the angled balloons can be substantially straightened to facilitate their insertion into the vessel of the patient.

Another object of the invention is to provide a dilatation catheter and above of the above character in which various angles can be achieved.

Another object of the invention is to provide a dilatation catheter in which markers are provided.

Another object of the invention is to provide a dilatation catheter of the above character in which directional markers are provided to indicate the orientation of the balloon in the vessel in the patient.

Additional objects and features of the invention will appear from the following description in which the preferred embodiments are set forth in detail in conjunction with the accompanying drawings.

FIG. 1 is a side elevational view partially in cross section of a dilatation catheter having angled balloon incorporating the present invention and having an angled protective sleeve on the angled balloon.

FIG. 2 is a cross-sectional view taken along the line 2—2 of FIG. 1.

FIG. 3 is an enlarged cross-sectional view of the distal extremity of the catheter shown in FIG. 1 but without a guide wire extending through the same.

FIG. 4 is a view similar to that shown in FIG. 3 but with a guide wire extending through the balloon.

Figure 5:
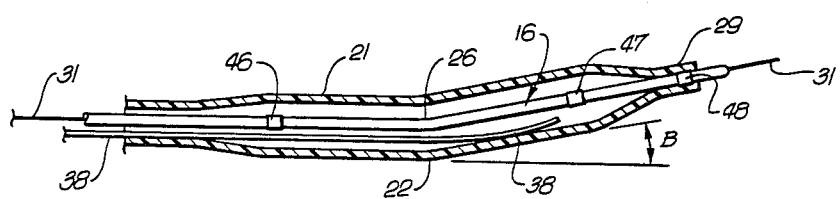
FIG. 5 is a view similar to that shown in FIG. 3 but showing the angled balloon straightened out in a manner so that it can be inserted into the vessel of the patient.

In general, the dilatation catheter with angled balloon consists of a flexible elongate tubular member having first and second lumens extending therethrough and having proximal and distal extremities. An angled balloon is carried by the distal extremity of the tubular member. The elongate tubular member includes a tubular element which extends through the balloon and has the first lumen extending therethrough. The first lumen is of a size that is capable of receiving a guide wire so that a guide wire can extend through the balloon. Means is provided for establishing communication between the second lumen and the interior of the balloon for inflating and deflating the balloon. The balloon has a configuration so that when it is inflated it will subtend a suitable angle ranging from about 35° or less to about 160° or more.

More particularly, the dilatation catheter 11 of the present invention consists of a flexible elongate tubular member 12 which carries first and second lumens or flow passages 13 and 14 which extend therethrough. The lumens or flow passages 13 and 14 can be provided in a suitable manner, as for example, extruding the tubular member 12 so it is provided with two of such passages extending longitudinally of the same. Alternatively, as shown in FIG. 2, the two flow passages 13 and 14 can be provided with a first lumen or flow passage 13 which extends through an inner tubular member 16 and in which the second lumen or flow passage 14 is formed by an annular flow passage or lumen 14 extending between the outer surface of the inner tubular member 16 and the inner surface of an outer tubular member 17. The tubular member 12, if formed with this co-axial construction can be formed in the manner described in U.S. Pat. No. 4,323,071. By way of example, the inner tubular member 16 can be formed of a suitable plastic such as polyester or polyolefin. The outer tubular member 17 also can be formed of a polyolefin or a polyester.

By way of example, the outer tubular member 17 can have suitable dimensions such as an inside diameter of 0.046 inch with an outside diameter varying from 0.056 to 0.057 inch. In this example the inner tubular member 16 can have a suitable inner diameter such as 0.020 inch and an outer diameter of 0.035 inch. However, it should be understood that larger or smaller tubular members can be employed, if desired. The outer tubular member can, for example, have an outer diameter as large as 0.064 inch or as small as 0.020 inch.

An angled balloon 21 is carried by the distal extremity of the tubular member 12. The angled balloon 21 can be formed with a bend 22 so that the interior angle subtends an angle A ranging from about 35° or less to about 160° or more. Such an angled balloon can be made in several different ways. By way of example, the balloon can be first formed in a mold, as for example, a glass mold which has the desired configuration for the balloon. Alternatively, if it is not desired to utilize a mold, the balloon can be formed in the conventional 180°, or straight, configuration and then heat treating the same, as for example, by the use of a heated air or a heated solid coming into contact with the balloon material at an appropriate area to form the desired angle by introducing shrinkage in that area of the balloon. Since it is often desirable to form a balloon which has an angle of approximately 90° with the guide wire inserted into the same, it is desirable to form the balloon with a lesser angle, as for example, 45° as shown in FIG. 3 to accommodate forces applied on the balloon by the guide wire when the guide wire is inserted into the first lumen and extends through the first lumen and particularly through the portion of the first lumen which extends through the angled balloon.

The angled balloon 21 is formed of a suitable polymeric material such as a polyester which can be formed with very thin walls of great strength. This material can be extruded and blown to form an angled balloon. By way of example, such a balloon can have an outside diameter, as for example, ranging from about 1.5 to about 4.0 millimeters. Such a balloon can have a wall thickness as thin as 0.001 inch and still be inflated to pressures in the range of 10 to 15 atmospheres. If desired, the inner tubular member 16 also can be provided with a bend 26 of the same angle as the bend 22 provided for the angled balloon.

The angled balloon 21, after it has been formed, can be secured to the distal extremity of the tubular member 12. If a separate balloon is used rather than an integral balloon, the proximal portion 28 of the balloon can be necked down and secured to the distal extremity of the outer tubular member 12 by suitable means such as an adhesive or by heat if irradiated plastic is used for the balloon. The distal extremity 29 of the balloon is also necked down and can be secured to the distal extremity of the inner tubular member 16 by a shrink fit or, alternatively, by the use of an adhesive.

As can be seen from the construction shown, means is provided in the form of the first lumen or flow passage 13 having an inside diameter of 0.020 inches extending through the inner tubular member 16 which is adapted to receive a guide wire 31 of a conventional type, as for example, the 0.018 "Hi-Torque Floppy" (trademark) guide wire manufactured and sold by Advanced Cardiovascular Systems, Inc., of Mountain View, Calif. As can be seen from the construction shown in FIG. 4, means is provided for establishing communication between the second lumen or flow passage 14 and the interior of the angled balloon 21 so that the balloon can be inflated and deflated as hereinafter described. The distal extremity of the inner tubular member 16 can be rounded as shown and can be relatively soft. The distal extremity can have a maximum diameter of, for example, 0.045 inches and a length of approximately 9 millimeters. The balloon itself can have a length of 10-50 millimeters and preferably approximately 30 millimeters with 15 millimeters being provided on each side of the bend 22.

A three-arm adapter 36 is mounted on the proximal extremity of the tubular member 12. The side arm 37 of the adapter 36 is adapted to receive a vent tube 38 for venting air from the balloon 21 as it is inflated. The center arm 39 is in communication with the first lumen or flow passage 13 which extends completely through the dilatation catheter 11 and particularly through the balloon 21. Another side arm 41 is provided which is in communication with the second lumen or flow passage 14 and serves as a port for introducing a liquid medium for inflating and deflating the angled balloon 21.

Suitable means is provided for ascertaining the position of the balloon in the distal extremity of the catheter 11 when it is being used in an angioplasty procedure and consists of radiopaque markers. For example, as shown in FIG. 1, a pair of radiopaque markers 46 and 47 can be provided within the balloon on the tubular member 16 adjacent to the proximal and distal extremities of the balloon. An additional marker 48 can be provided adjacent the tip of the inner tubular member 16. The radiopaque markers 46, 47 and 48 can be in a suitable form, as for example, gold bands.

In making the angled balloon 21, it is desirable to form the angled balloon with an angle A which is less than the desired angle, as for example, 45° as shown in FIG. 3. This is because when the guide wire 31 is inserted through the balloon as is shown in FIG. 4, the guide wire will decrease the angle of the bend, as for example, by changing the angle of the balloon from approximately 45° to approximately 85°. In order to make it easier to insert the angled balloon into the vessel, it is sometimes necessary to straighten the balloon in some suitable manner. One way to accomplish this is to make a vent tube 38 stiff enough to provide the desired degree of straightening when it is inserted to the distal extremity of the balloon. The relatively stiff vent tube has a tendency to remain essentially straight and this tube and the guide wire acting together can straighten the balloon so it only subtends a small angle B (see FIG. 5), e.g., 0° to 15°, with the axis of the catheter shift. If desired, in order to obtain sufficient straightening of the balloon, a stiffer guide wire can be utilized until the balloon has advanced to a location near the stenosis. The stiff guide wire can be removed and a more flexible guide wire exchanged therefor and inserted into the balloon.

In order to retain the desired bend in the balloon 21 during shipment and storage before use of the catheter 11, an angled sleeve 49 is provided which is slipped over the balloon 21 and is frictionally retained thereon. The sleeve has a length slightly greater than the length of the balloon 21. The sleeve can be formed of plastic having a wall thickness so that the sleeve is relatively rigid. Thus, the sleeve 49 will retain the balloon at the desired angle during shipment and sterilization and storage. This ensures that the balloon 21 will have the desired angle when the catheter 11 is used.

Operation and use of the dilatation catheter 11 with angled balloon in performing the present method may now be briefly described as follows. Let it be briefly assumed that it is desired to open a difficult stenosis which extends around an angle in an arterial vessel of a patient. A catheter with an angled balloon is selected. A vent tube 38 is positioned in the balloon so that its distal extremity is near the distal extremity of the balloon. The balloon 21 is filled in a conventional manner by introducing radiographic contrast liquid through the inflation port 41. As the liquid enters the interior of the angled balloon 21, the air in the balloon will be pushed forward and will be vented to atmosphere through the vent tube 38. The balloon 21 is then deflated by withdrawing the radiographic contrast liquid therefrom and maintaining a vacuum within the balloon. The vent tube is then withdrawn so that its distal end is near the proximal end of the balloon unless it is being utilized to straighten the balloon, in which case it is positioned as desired to provide the desired degree of straightening. Thereafter a guide wire 31 is selected and introduced through the first lumen 13 and through the angled balloon 21 as shown in FIG. 4 so that the balloon with the guide wire therein assumes a conformation with the desired angle. If this angle is approximately 85° to 90°, assuming that is the angle desired by the physician performing the angioplasty procedure, frictional means may thereafter be inserted to further straighten the balloon so that it can be inserted into the vessel. As explained previously, this can be accomplished by utilizing the vent tube or a stiffer guide wire to straighten the angled balloon. After the balloon has been strightened to the angle B of 0° to 15° from the catheter shaft, it can be advanced into the vessel of the patient into the region of the stenosis by first advancing the guide wire 31 in the vessel and then advancing the dilatation catheter 11 on the guide wire until it reaches the stenosis. After the stenosis has been reached and it is desired to have the balloon assume an angled conformation, as for example, approximately 90°, the vent tube 38 can be withdrawn permitting the balloon to gradually assume its angled condition and to permit it to be advanced into and through the stenosis. After it is ascertained by observing the markers on the catheter that the balloon had been advanced sufficiently far, the balloon can be inflated by the introduction of a radiographic contrast liquid into the inflation port 41. After the stenosis has been enlarged, the angled balloon can be deflated and the dilatation catheter 11 and the guide wire 31 removed from the vessel in a conventional manner.

It has been found that in many cases, regardless of the orientation of the balloon 21 and its angle, when the balloon is inflated it will assume the conformation of the vessel in which it is disposed so that it will assume an angular position which corresponds to the angular position of the stenosis. This makes it unnecessary to rotate the distal extremity of the catheter so that the angular balloon has the desired angularity with respect to the stenosis.

Figure 6:
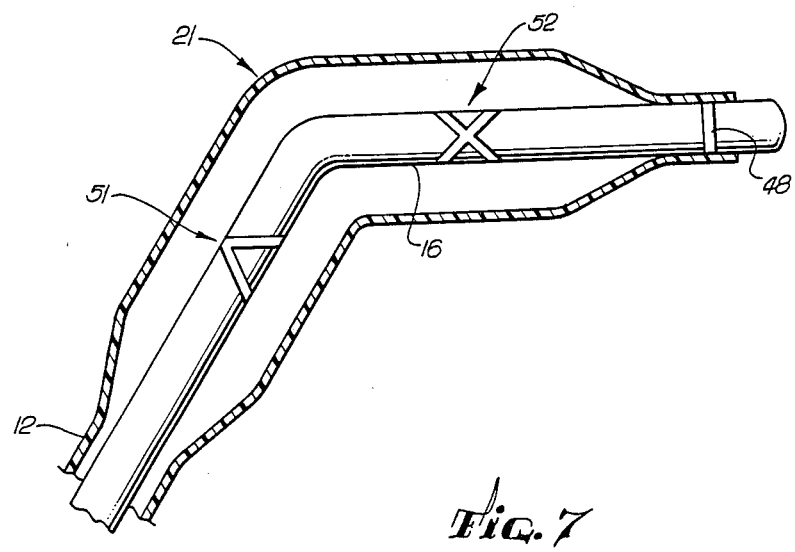
FIG. 6 is an enlarged side elevational view of the distal extremity of another embodiment of a dilatation catheter with angled balloon carrying directional markers.
Figure 7:
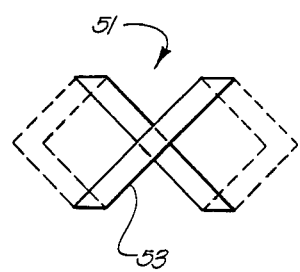
FIG. 7 is a further enlargement of one of the directional markers shown in FIG. 6.

If it is desired to more closely track the angular position of the angled balloon 21, suitable spaced apart markers 51 and 52 can be placed within the balloon 21 (see FIG. 6) to make it possible for the physician viewing the balloon 21 under a fluoroscope to ascertain its angular position before inflation of the same. The markers 51 and 52 can be provided on the inner tubular member 16 within the balloon adjacent the proximal and distal extremities of the balloon 21. The markers 51 and 52 have a distinctive relationship to the angular position of the balloon. The markers 51 and 52 are formed of a suitable material such as gold ribbon 53 with a suitable width such as 0.010 inch and a thickness of 0.002 inch, which is wrapped onto a mandrel (not shown) to form a double helix as shown in FIG. 7 by the solid and broken lines. A solder joint can be formed at the overlap of the gold ribbon. The ribbon 53 is trimmed and the markers 51 and 52 are then removed from the mandrel. The first double helix band or marker 51 is placed in an angular position on the inner member 16. The second double helix band or marker 52 is placed on the inner tubular member rotated by 90° from the position of the first band 51. Each of these double bands 51 and 52 can be fastened to the inner tubular member 16 by suitable means such as an adhesive. By observing the positions of the first and second bands 51 and 52 under fluoroscope, it is relatively easy for the physician to ascertain the rotational position of the angled balloon with respect to the stenosis. If the angled balloon is improperly rotated, the angled balloon can be rotated to the desired angular position by rotating the main shaft of the catheter 11 provided by the tubular member 12. By observing the relationship between the first and second markers or bands 51 and 52, the physician can ascertain relatively precisely the position of the angled balloon. This is particularly desirable prior to inflation of the angled balloon 21 in the vessel.

While the invention has been described with reference to a catheter having a separate vent tube for the balloon, it can also be employed with a self venting catheter having a small channel or a plurality of small holes which permit the passage of air but not liquid inflation medium from the balloon.

It is apparent from the foregoing that there has been provided a dilatation catheter and method utilizing an angled balloon which makes it possible to treat what in the past has been considered to be inoperable stenoses and still to enlarge the same in a relatively simple angioplasty procedure. Because of the construction provided, it is possible for the physician to relatively precisely position the balloon of the dilatation catheter before dilating the balloon.

What is claimed is:

1. A balloon catheter comprising a flexible, elongate tubular member having at least one lumen extending therethrough and having proximal and distal extremities, an inflatable balloon which is carried by the distal extremity of the tubular member and which is preformed to subtend a predetermined interior angle between about 35° and 160° when inflated, a tubular element extending at least through the balloon interior which is preformed to subtend a predetermined interior angle between about 35° and 160° and which is adapted to receive a guide wire therethrough, and means for establshing fluid communication between a lumen in the tubular member and the interior of the balloon for inflating and deflating the balloon.

2. The catheter of claim 1 including a guide wire disposed in and extending through the tubular element to yieldably increase the angle subtended by the balloon.

3. The catheter of claim 1 including an additional elongate member extending through a lumen in the tubular member into the interior of the balloon to apply an additional yieldable force to further increase the interior angle subtended by the balloon.

4. The catheter of claim 3 in which said additional elongate member is a vent tube extending through a lumen in the tubular member.

5. The catheter of claim 1 in which the inflated balloon subtends an interior angle of about 35° to about 160°.

6. The catheter of claim 1 including spaced apart directional markers carried by the tubular element within the balloon, each of the markers having a different angular position with respect to the other markers.

7. The catheter of claim 6 in which said markers are in the form of a double helix of a radiopaque material.

8. The catheter of claim 1 in which the subtended angle is approximately 85°.

9. The catheter of claim 2 including a removable angled sleeve disposed on and frictionally engaging the exterior of the uninflated balloon to retain the predetermined angle in the balloon when inflated.

10. The catheter of claim 1 wherein the balloon is preformed to subtend a predetermined interior angle when inflated.

11. The catheter of claim 1 wherein the tubular element is preformed to subtend essentially the same interior angle as the inflated balloon.

12. A method for utilizing a catheter with a balloon on the distal portion thereof which is preformed to subtend a predetermined angle when inflated, a guide wire, and a vent tube, said method comprising, advancing the guide wire through the dilatation catheter to straighten the angled balloon of the catheter, inserting the guide wire into a vessel of a patient, moving the dilatation catheter over the guide wire, advancing the guide wire so that it extends through the stenosis and advancing the angled balloon over the guide wire into the stenosis, inflating the angled balloon while it is positioned in the stenosis, deflating the balloon and thereafter removing the balloon dilatation catheter and the guide wire from the vessel.

13. A method as in claim 12 together with the step of observing the orientation of the angled balloon after it has been inflated in the stenosis to ascertain whether it has a desired orientation in the stenosis, deflating the angled balloon if the angled balloon does not have the desired orientation in the stenosis, rotating the balloon dilatation catheter so that the angled balloon has the desired orientation in the stenosis and thereafter inflating the angled balloon in the stenosis.

14. A method as in claim 13 wherein the orientation of the balloon dilatation catheter is fluoroscopically detected by means of axially spaced apart markers in the balloon, each of the spaced apart markers on the balloon having a different fluoroscopically decernable angular relationship with respect to another marker.

15. A method of claim 14 including the step of inserting a flexible, relatively stiff element into a lumen within the catheter until it extends into the balloon and straightens the balloon so that it can be advanced into the vessel, and removing the relatively stiff element when said angled balloon has reached a position in proximity to the stenosis.

* * * * *